United States Patent
Beucher (10) Patent No.: US 10,702,227 B2
(45) Date of Patent: Jul. 7, 2020

(54) METHOD OF RADIOGRAPHY OF AN ORGAN OF A PATIENT

(71) Applicant: EOS IMAGING, Paris (FR)

(72) Inventor: Jérôme Beucher, Esbly (FR)

(73) Assignee: EOS IMAGING, Paris (FR)

( * ) Notice: Subject to any disclaimer, the term of this patent is extended or adjusted under 35 U.S.C. 154(b) by 33 days.

(21) Appl. No.: 16/076,660

(22) PCT Filed: Feb. 10, 2016

(86) PCT No.: PCT/IB2016/000273
§ 371 (c)(1),
(2) Date: Aug. 8, 2018

(87) PCT Pub. No.: WO2017/137792
PCT Pub. Date: Aug. 17, 2017

(65) Prior Publication Data
US 2019/0046133 A1    Feb. 14, 2019

(51) Int. Cl.
*A61B 6/02* (2006.01)
*A61B 6/00* (2006.01)
(Continued)

(52) U.S. Cl.
CPC ............ *A61B 6/4014* (2013.01); *A61B 6/02* (2013.01); *A61B 6/022* (2013.01); *A61B 6/4007* (2013.01);
(Continued)

(58) Field of Classification Search
CPC .. A61B 6/02; A61B 6/022; A61B 6/40; A61B 6/4014; A61B 6/44; A61B 6/4429; A61B 6/4435
See application file for complete search history.

(56) References Cited

U.S. PATENT DOCUMENTS

| | | | |
|---|---|---|---|
| 4,811,372 A * | 3/1989 | Doebert | A61B 6/14 378/38 |
| 6,104,780 A | 8/2000 | Hanover et al. | |

(Continued)

FOREIGN PATENT DOCUMENTS

| | | |
|---|---|---|
| CN | 104095643 A | 10/2014 |
| EP | 0 917 856 A1 | 5/1999 |

(Continued)

OTHER PUBLICATIONS

International Search Report, dated Nov. 8, 2016, from corresponding PCT application No. PCT/IB2016/000273.

*Primary Examiner* — Thomas R Artman
(74) *Attorney, Agent, or Firm* — Young & Thompson (57) ABSTRACT

Disclosed is a method of radiography of an organ of a patient, including: a first vertical scanning of the organ by a first radiation source and a first detector cooperating to make a first two dimensional image of the organ, a second vertical scanning of the organ by a second radiation source and a second detector cooperating to make a second two dimensional image of the organ, the first vertical scanning and the second vertical scanning being performed synchronously, the first and second images viewing the organ of the patient according to different angles of incidence, wherein there is a vertical gap between the first source/detector and the second source/detector, such that the first vertical scanning and the second vertical scanning are performed synchronously but with a time shift in between, so as to reduce cross-scattering between the first and second images.

24 Claims, 3 Drawing Sheets

(51) Int. Cl.
    *A61B 6/03*     (2006.01)
    *A61B 6/06*     (2006.01)
(52) U.S. Cl.
    CPC ............... *A61B 6/025* (2013.01); *A61B 6/03* (2013.01); *A61B 6/06* (2013.01); *A61B 6/4435* (2013.01)

(56) References Cited

U.S. PATENT DOCUMENTS

| | | | |
|---|---|---|---|
| 6,735,274 B1 * | 5/2004 | Zahavi | A61B 6/032 378/15 |
| 7,224,764 B2 * | 5/2007 | Sukovic | A61B 6/032 378/19 |
| 9,245,658 B2 | 1/2016 | Desaute | |
| 2003/0076920 A1 | 4/2003 | Shinno et al. | |
| 2005/0175143 A1 * | 8/2005 | Miyazaki | A61B 6/032 378/19 |
| 2009/0080598 A1 | 3/2009 | Tashman et al. | |
| 2009/0207968 A1 | 8/2009 | Grass | |
| 2019/0046133 A1 * | 2/2019 | Beucher | A61B 6/022 |

FOREIGN PATENT DOCUMENTS

| | | |
|---|---|---|
| EP | 2309462 A2 | 4/2011 |
| JP | H03-24300 U | 3/1991 |
| JP | H05-168616 A | 7/1993 |
| JP | 2009-297314 A | 12/2009 |
| JP | 2010-124832 A | 6/2010 |
| JP | 2013-525053 A | 6/2013 |
| WO | 99/30615 A1 | 6/1999 |
| WO | 2005/006986 A1 | 1/2005 |
| WO | 2011/138632 A1 | 11/2011 |

* cited by examiner

FIG. 3

METHOD OF RADIOGRAPHY OF AN ORGAN OF A PATIENT

FIELD OF THE INVENTION

The invention relates to methods of radiography of an organ of a patient, as well as associated apparatus, in particular when the patient is an overweight or obese patient. In particular, this method of radiography is preferably a stereo-radiography method.

BACKGROUND OF THE INVENTION

The field of the invention deals with a double scanning, preferably stereo-radiographic, system and a method to optimize the radiation, preferably x-ray, scattering rejection and correction in order to acquire at least two simultaneous views, preferably frontal and lateral view images for low dose three dimensional reconstruction of an organ, preferably the skeleton, of patients for medical applications.

This system and method are dedicated to be used within medical radiology devices including at least two radiation, preferably x-ray, transmissions based imaging capabilities. These capabilities will be based on for example at least an x-ray emission source emitting x-ray spectra having a higher energy comprised between 20 keV and 200 keV. The typical imaged object is a patient in weight bearing position.

A scanning stereo-radiographic system such as the one described in EP 2309462 demonstrated good capabilities to make simultaneous frontal and lateral images for three dimensional reconstruction of skeletal anatomical parts such as the rachis or pelvis with a dose reduction up to 600 compared to Computed Tomography scan, and also a dose reduction up to 10 for single view images compared to Computed Radiography or Digital Radiography systems. But the maximum available dose rate of this system has also become a growing limitation to produce enough clinical quality images of overweight and obese patients, all the more that overweight and obese patients are nowadays very common patients.

One important problem to make some good clinical quality radiology images on overweight and obese patients is the big amount of scattered x-rays created while the direct x-ray beam is much attenuated. Thus, the transmitted direct x-ray signal can become very small, typically 10-20 times lower, in comparison with the scattered x-ray signal in direct two dimensional imaging systems.

Some scattering rejection grids are commonly used to solve this problem, but taken alone, their efficiency is not good enough, and therefore the dose on overweight and obese patients can become very high in order to get clinical quality images.

A scanning stereo-radiographic system such as the one described in EP 2309462 demonstrates an efficient scattered x-ray rejection using a very thin object and detector collimations. But the useful dose rate fraction to make the image becomes too small for overweight patients. Some of the reasons are the limited output power of x-ray tubes and the very small collimation apertures.

According to such a prior art, for example described in EP 2309462, there is described a radiology method performing vertical scanning. This radiology method used collimators located upstream detectors, thereby improving cross-scattering and self-scattering rejection. However, high rejection rate was achieved thanks to narrow collimation thereby at the expense of lowering much the level of received radiation signal on the sensitive surfaces of the detectors. Therefore, at least for some patient organs, when used with reasonably overweight patients, it was difficult, and when used with really overweight or even obese patients, it was not possible, to find a good compromise between a high rate of scattering rejection and simultaneously a sufficient level of received radiation signal on the sensitive surfaces of the detectors.

A system to tune the aperture of the collimation according to the patient morphology such as the one described in another prior art, for example described in WO 2011/138632, could be used to enhance the ability to make clinical quality images on overweight patients of the scanning stereo-radiographic system described in EP 2309462.

But, in this case, the output power of the x-ray tube and available collimation aperture of the detector would not be enough to cover the whole growing population of the varied morphologies among overweight and obese patients. The aperture limitation will be directly linked with the loss of spatial resolution of the detector and the amount of scattered x-ray coming from both x-ray imaging frontal and lateral views. The use of coplanar simultaneous frontal and lateral x-ray views will create a specific problem of cross-scattering in addition to the self-scattering pollution of each view.

SUMMARY OF THE INVENTION

The object of the present invention is to alleviate at least partly the above mentioned drawbacks.

More particularly, the invention aims at providing for a radiology method which allows, for all or most of types of patient organ, for all or most types of patient morphology, including overweight and preferably obese patients, for simultaneously achieving both a received signal level on sensitive surfaces of detectors sufficiently high and a cross-scattering rejection rate sufficiently high, so as to get a good signal to noise ratio and a good image quality.

Therefore, the invention provides for a vertical gap between first and second vertical scanning reducing, preferably drastically reducing with the help of collimation tunnels located upstream detectors, at least the cross-scattering between first and second images.

Embodiments of the invention are dedicated to enhance greatly the capability to make improved and good clinical quality images of simultaneous frontal and lateral views on standard patients and on overweight and obese patients, improving both spatial resolution, Signal to Noise Ratio and contrast of images while simultaneously reducing the image quality loss due to cross-scattered and self-scattered radiation, preferably x-ray radiation.

This object is achieved with a method of radiography of an organ of a patient, comprising: a first vertical scanning of said organ by a first radiation source and a first detector cooperating to make a first two dimensional image of said organ, a second vertical scanning of said organ by a second radiation source and a second detector cooperating to make a second two dimensional image of said organ, said first vertical scanning and said second vertical scanning being performed synchronously, said first and second images viewing said organ of said patient according to different angles of incidence, wherein said method of radiography is performed with an overweight patient or with an obese patient, and wherein a first collimation tunnel is located upstream said first detector, a second collimation tunnel is located upstream said second detector, there is a vertical gap between on the one hand said first source and detector and on the other hand said second source and detector, such that said first vertical scanning and said second vertical scanning are performed synchronously but with a time shift in between, so as to reduce cross-scattering between said first and second images.

When the cross-scattering level is not that high or when one can afford a high vertical gap, not being limited by a too low threshold for the total height of the apparatus, this object will also be achieved with a method of radiography of an organ of a patient, comprising: a first vertical scanning of said organ by a first radiation source and a first detector cooperating to make a first two dimensional image of said organ, a second vertical scanning of said organ by a second radiation source and a second detector cooperating to make a second two dimensional image of said organ, said first vertical scanning and said second vertical scanning being performed synchronously, said first and second images viewing said organ of said patient according to different angles of incidence, wherein there is a vertical gap between on the one hand said first source and detector and on the other hand said second source and detector, such that said first vertical scanning and said second vertical scanning are performed synchronously but with a time shift in between, so as to reduce cross-scattering between said first and second images.

The time shift corresponds to said second vertical scanning arriving at each height of said organ after said first vertical scanning, with a given delay, or vice-versa.

Different angles of incidence correspond to different directions (which are then not parallel), as for example two perpendicular directions, corresponding for example to a frontal view and to a lateral view of patient organ.

This object is still achieved with a radiography apparatus comprising: a first radiation source and a first detector cooperating to make a first two dimensional image of an organ of a patient, by performing a first vertical scan of said organ of said patient, a second radiation source and a second detector cooperating to make a second two dimensional image of said organ of said patient, by performing a second vertical scan of said organ of said patient, said sources and said detectors cooperating so as to perform said first vertical scanning and said second vertical scanning synchronously, said first and second images viewing said organ of said patient according to different angles of incidence, wherein there is a vertical gap between on the one hand said first source and detector and on the other hand said second source and detector, such that said first vertical scanning and said second vertical scanning are performed synchronously but with a time shift in between, so as to reduce cross-scattering between said first and second images.

Preferred embodiments comprise one or more of the following features, which can be taken separately or together, either in partial combination or in full combination, in combination with either object of the invention previously presented.

Preferably, said method of radiography is performed with an overweight patient or with an obese patient.

The method of radiography according to the invention is all the more interesting that the cross-scattering level is high. Therefore, with overweight or even obese patient, the cross-scattering level being quite high, this method of radiography becomes very interesting.

Preferably, a collimation tunnel is located upstream each detector so as to further reduce cross-scattering on each image.

Preferably, there are a first collimation tunnel located upstream said first detector so as to further reduce cross-scattering between said first and second images, and a second collimation tunnel located upstream said second detector so as to further reduce cross-scattering between said first and second images.

That way, the cross-scattering level is further reduced because of the cooperation between the vertical gap of both radiation beams and the effective aperture reduction of both detectors. Indeed, by reducing the effective aperture of both detectors, the effect of the vertical gap between both beams is amplified, and a limited vertical gap will already result in an important cross-scattering level drop.

Preferably, said collimation tunnel has a depth of more than 20 mm, preferably more than 40 mm.

The longer the depth of the collimation tunnel is, the better the reduction of cross-scattering level is.

Preferably, said vertical gap is less than 100 mm, preferably less than 80 mm, more preferably less than 60 mm.

The shorter the depth of the collimation tunnel, the more important the available space for the patient within the cabin and the most useful the scanned width on the patient.

Therefore a compromise has been found between on the one hand the reduction of cross-scattering level and on the other hand raising the useful part of the scanned width on the patient as well as maintaining a sufficiently important available space for the patient within the cabin. This compromise ranges from 20 mm to 100 mm, and an even better compromise ranges from 40 mm to 60 mm.

There is also an interaction between the value of the vertical gap and the depth of the collimation tunnels by the detectors. So, these compromises are all the better that the vertical gap best ranges disclosed by the invention are used.

Preferably, no scattering rejection grid is located upstream any detector.

The disposition of collimation tunnels upstream detectors not only reduces cross-scattering between first and second images, but also reduces by the way self-scattering on both first and second images, thereby allowing for removing usually existing scattering rejection grids located upstream detectors. That way, presence of collimation tunnels upstream detectors allows for a triple benefit which is, first reducing cross-scattering, second reducing self-scattering, and third removing scattering rejection grids.

Preferably, said vertical gap is more than the height of the sensitive surface of any of the detectors, preferably more than twice said height, more preferably more than four times said height.

That way, the big size of the vertical gap relatively to the vertical size of the sensitive surface of the detectors will ensure that very little cross-scattering between first and second images happen indeed.

Preferably, said vertical gap is more than 10 mm, preferably more than 20 mm, more preferably more than 30 mm.

The bigger the vertical gap, the better the reduction of cross-scattering level.

Preferably, said vertical gap is less than 100 mm, and more preferably less than 60 mm, having for example a preferred range from 20 mm to 50 mm, so that the delay between both vertical scanning is limited, so that the patient may not move significantly during this delay, so that a good correspondence between both first and second images is kept, so that a good quality of the global three dimensional reconstruction from both first and second images is kept.

Preferably, a height of the sensitive surface of both detectors ranges from 2 mm to 8 mm, preferably ranges from 3 mm to 6 mm.

That way, a good compromise, between a sufficient effective aperture of the detectors to ensure a sufficient level of signal received by detectors and a not too important effective aperture of the detectors to avoid a too high level of cross-scattering between first and second images, is met.

Preferably, said vertical gap is fixed.

In this embodiment, simplicity of the radiology mechanism required to allow for this synchronous although timely shifted scanning prevails.

Preferably, said vertical gap is tunable.

Preferably, said vertical gap is tunable according to patient morphology and/or according to patient organ.

Preferably, said vertical gap is tunable according to respective effective apertures of said sources and according to respective effective apertures of said detectors, which said effective apertures are in turn tunable according to patient morphology and/or according to patient organ.

In this other embodiment, flexibility of the radiology method performance, useful to cover many different possible situations with respect to patient morphology as well as with respect to patient organ, prevails.

Preferably, said vertical gap does not exist at the very beginning of said first vertical scanning, but does exist at the very beginning of said second vertical scanning, and said vertical gap does not exist at the very end of said second vertical scanning, but does exist at the very end of said first vertical scanning.

In this embodiment, both first and second vertical scanning follow exactly the same vertical course but follow it with a delay between each other. When not in use, the first source and detector on one side and the second source and detector on the other side, are both at the same vertical height. There is then the advantage of keeping lower the total required height for the global required vertical course which is equal to each one of the courses needed for the first and second vertical scanning. This way, the global height of the required moving mechanism, as well as the total height of the radiology apparatus, will be lower.

Preferably, said vertical gap does always exist, even when neither said first vertical scanning nor said second vertical scanning are performed.

In this other embodiment, both first and second vertical scanning follow the same vertical course only on major part of it, neither at the very beginning nor at the very end; besides, they follow it with a delay between each other. When not in use, the first source and detector on one side and the second source and detector on the other side, are not at the same vertical height. There is then the advantage of allowing for a mechanically simpler system to ensure a permanent vertical gap between the first source and detector on one side and the second source and detector on the other side. This way, the structure of the global required moving mechanism, as well as the structure of the whole radiology apparatus, will be simpler.

Preferably, said patient morphology is chosen by a user of said method of radiography, preferably among a discrete number of choices.

In this embodiment, choosing the type of patient morphology, as well as the type of patient organ, is let to the practitioner. This manual choice makes the whole system simpler, but requires a supplementary step from the practitioner, and may be the cause of a possible although improbable error.

Preferably, said patient morphology is determined by a scout view scanning at a reduced level of radiation.

In this other embodiment, choosing the type of patient morphology is performed automatically by using a kind of preview scanning at very low radiation dose. This automatic choice makes the whole system a bit more sophisticated, but avoids a supplementary step from the practitioner thereby making the system as a whole more secure, an error from the practitioner remaining always a possibility even if mostly improbable.

Besides, making available a scout view allows for not only choosing the type of patient morphology via his thickness, but also his maximal thickness at each vertical height and for each image of the organ. Thereby, not only can tension and filtering function be chosen, but also the value of the current within the tubes of the sources.

Preferably, said detectors are geometrically linear detectors, and said detectors are preferably geometrically multi-lines linear detectors. A geometrically linear detector is a detector having a single row or several rows of aligned elementary detection units. A geometrically multi-lines linear detector is a detector having several, at least two, parallel rows of aligned elementary detection units. The multi-lines linear detector may have an output signal which is either a linear function of its input signal or a non-linear function of its input signal.

That way, both the scanning image pixels dynamics and the image signal to noise ratios are improved. Yet, performing the considered vertical scanning with one line detectors, this single line being in a horizontal plan, remains possible.

The used detectors present a few detection lines, typically 1 up to 100 lines, that can be used to acquire some frame images or can be summed according to a specified TDS (Time Delay Summation) or TDI (Time Delay Integration) speed in order to get a higher scanning image pixels dynamics and Signal to Noise Ratio. The effective aperture of such a detector is therefore higher than a single line detector, typically ranging from 0.1 up to 10 mm. This feature of TDS or TDI mode often provides a significant improvement in clinical quality image in comparison to detectors equipped with only one detection line for the same x-ray source output power. Other types of detectors can be used too, like for example 2D detectors. The detector may be either a solid or a gaseous detector, whether 1D or 2D detector.

Preferably, collimators are located downstream said sources.

That way, making the emitted radiation beams more collimated, that is more directional, the global level of scattering, either cross-scattering or self-scattering, may be further reduced.

Preferably, said first and second images are perpendicular views of said organ, and are preferably frontal and lateral views.

Therefore, a more reliable three dimensional modelling of the patient organ may be reconstructed from both these first and second images.

Preferably, said radiation sources are x-ray sources and said detectors are x-ray detectors.

Cross-scattering and self-scattering are particularly high with x-ray radiation, making the radiology method according to the invention, all the more interesting.

Cross-scattering between first and second images is the scattering on one image which comes from a signal dedicated to the other image. More precisely, radiation emitted by first source and scattered by patient organ in the specific direction which brings it on the sensitive surface of second detector, instead of first detector, is cross-scattered signal. The same way, radiation emitted by second source and scattered by patient organ in the specific direction which brings it on the sensitive surface of first detector, instead of second detector, is cross-scattered signal. These cross-scattered signals raise the noise level and therefore deteriorate the signal to noise ratio. Moreover, the cross-scattering deteriorates the spatial resolution, the contrast, the detection quantum efficiency (DQE) and other parameters.

Self-scattering on an image is the scattering on this image which comes from a signal dedicated to this image. More precisely, radiation emitted by first source and scattered by patient organ in the specific direction which brings it on the sensitive surface of first detector, as well as radiation scattered by the first detector itself, is self-scattered signal. The same way, radiation emitted by second source and scattered by patient organ in the specific direction which brings it on the sensitive surface of second detector, as well as radiation scattered by the second detector itself, is self-scattered signal. This self-scattered signal raises the noise level and therefore deteriorates the signal to noise ratio. Moreover, the self-scattering deteriorates the spatial resolution, the contrast, the detection quantum efficiency (DQE) and other parameters.

Further features and advantages of the invention will appear from the following description of embodiments of the invention, given as non-limiting examples, with reference to the accompanying drawings listed hereunder.

DETAILED DESCRIPTION OF THE INVENTION

Figure 1:
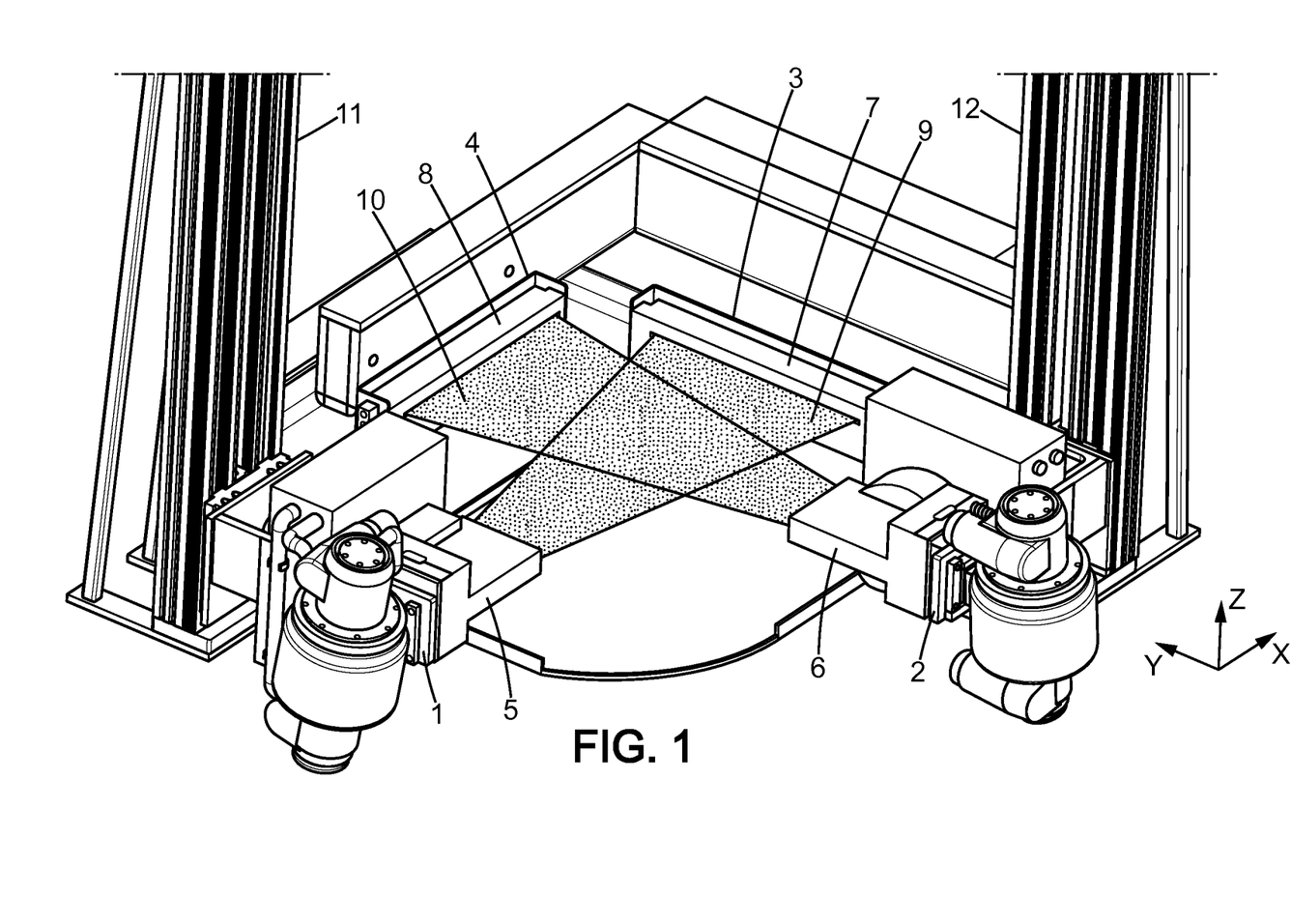
FIG. 1 shows an example of a radiology apparatus dedicated to performance of a radiology method, in which there is no vertical gap implemented between first and second vertical scanning, both first and second vertical scanning including collimation tunnels upstream the detectors, resulting in a still too high cross-scattering level.

FIG. 1 shows an example of a radiology apparatus dedicated to performance of a radiology method, in which there is no vertical gap implemented between first and second vertical scanning, both first and second vertical scanning including collimation tunnels upstream the detectors, resulting in a still too high cross-scattering level.

Patient will be in weight bearing position, which means patient will be standing vertically and not lying horizontally. Scanning will be performed in the vertical direction Z. Indeed, there will be both a frontal scanning giving a frontal image in the X direction and a lateral scanning giving a lateral image in the Y direction.

The radiology apparatus comprises two vertical slides 11 and 12. First vertical slide 11 is disposed for performing the frontal vertical scanning, whereas second vertical slide 12 is disposed for performing the lateral vertical scanning. Frontal vertical scanning will be performed along first vertical slide 11, whereas lateral vertical scanning will be performed along second vertical slide 12.

Along first vertical slide 11 will be translated first detection chain whereas along second vertical slide 12 will be translated second detection chain.

First detection chain comprises a first radiation source 1 associated to a first collimator 5 to narrow emitted beam 9 toward patient organ. After going through patient organ, not represented here for clarity reasons, the beam 9 enters in the first collimation tunnel 7 before reaching the sensitive surface of the first detector 3. Part of beam 9 is cross-scattered toward entering in the second collimation tunnel 8 before reaching the sensitive surface of the second detector 4. After end of first scanning, at the output of first detector 3 there is a first image, the frontal image of patient organ. The height of beam 9 considered is very small since it is the height of the beam 9 which will enter the first collimation tunnel 7 before reaching the sensitive surface of the first detector 3. Beam 9 may practically be considered as a planar beam.

Second detection chain comprises a second radiation source 2 associated to a second collimator 6 to narrow emitted beam 10 toward patient organ. After going through patient organ, not represented here for clarity reasons, the beam 10 enters in the second collimation tunnel 8 before reaching the sensitive surface of the second detector 4. Part of beam 10 is cross-scattered toward entering in the first collimation tunnel 7 before reaching the sensitive surface of the first detector 3. After end of second scanning, at the output of second detector 4 there is a second image, the lateral image of patient organ. The height of beam 10 considered is very small since it is the height of the beam 10 which will enter the second collimation tunnel 8 before reaching the sensitive surface of the second detector 4. Beam 10 may practically be considered as a planar beam.

Although a substantial part of cross-scattered signal is rejected, thanks to the presence of the collimation tunnels 7 and 8 located upstream the detectors 3 and 4, still a too important part of this cross-scattered signal is not rejected and manages to reach the sensitive surfaces of the detectors 3 and 4, thereby deteriorating the signal to noise ratio and the quality of both first frontal and second lateral images. Moreover, are also deteriorated the spatial resolution, the contrast, the detection quantum efficiency (DQE) and other parameters.

Either the tunnel collimations 7 and 8 are quite wide and the level of cross-scattering is too high, at least for overweight or obese patients, at least for some organs, or the tunnel collimations 7 and 8 are very narrow and the level of cross-scattering becomes acceptable, at least for overweight or obese patients, at least for some organs, but at the expense of a too low received signal on the sensitive surfaces of detectors 3 and 4.

Figure 2:
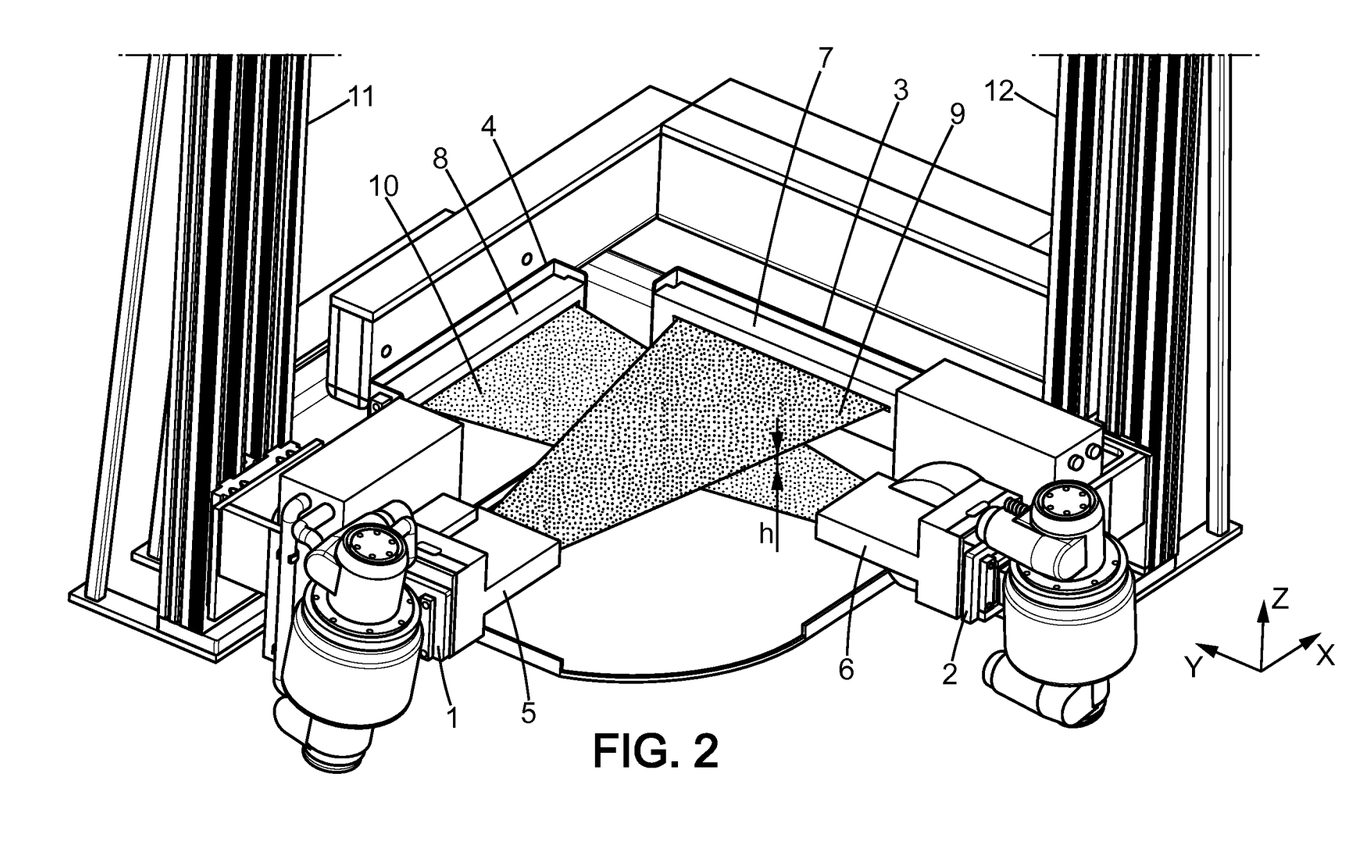
FIG. 2 shows an example of a radiology apparatus dedicated to performance of a radiology method, in which there is a vertical gap which has been implemented between first and second vertical scanning, both first and second vertical scanning including collimation tunnels upstream the detectors, resulting in a drastically reduced cross-scattering level.

FIG. 2 shows an example of a radiology apparatus dedicated to performance of a radiology method, in which there is a vertical gap which has been implemented between first and second vertical scanning, both first and second vertical scanning including collimation tunnels upstream the detectors, resulting in a drastically reduced cross-scattering level.

Here beams 9 and 10 are not at the same height with respect to each other. There is a vertical gap h between the heights of the middle plans of the beams 9 and 10. Thanks to this vertical gap h, the major part of cross-scattered signal which reached the sensitive surface of the detectors 3 and 4, will now be either stopped or deflected before, or may not even enter the collimation tunnels 7 and 8.

The beam 9 emitted by the first source 1, being narrowly collimated by the first collimator 5, will no more deflect any substantial cross-scattered signal toward the second collimation tunnel 8 and the second detector 4, thanks to the vertical gap h.

The beam 10 emitted by the second source 2, being narrowly collimated by the second collimator 6, will no more deflect any substantial cross-scattered signal toward the first collimation tunnel 7 and the first detector 3, thanks to the vertical gap h.

Both first and second detection chains will perform their respective scanning by respectively vertically sliding along first and second vertical slides 11 and 12, of patient organ to be imaged, either top down or bottom up.

Typical scanning speed may be about 7.5 cm per second, which makes, for a 190 cm height corresponding to 19000 lines, about 25 seconds of scanning time.

Maximal scanning speed may be close to 30 cm per second, which makes, for a 190 cm height corresponding to 19000 lines, about 6.3 seconds of scanning time.

Figure 3:
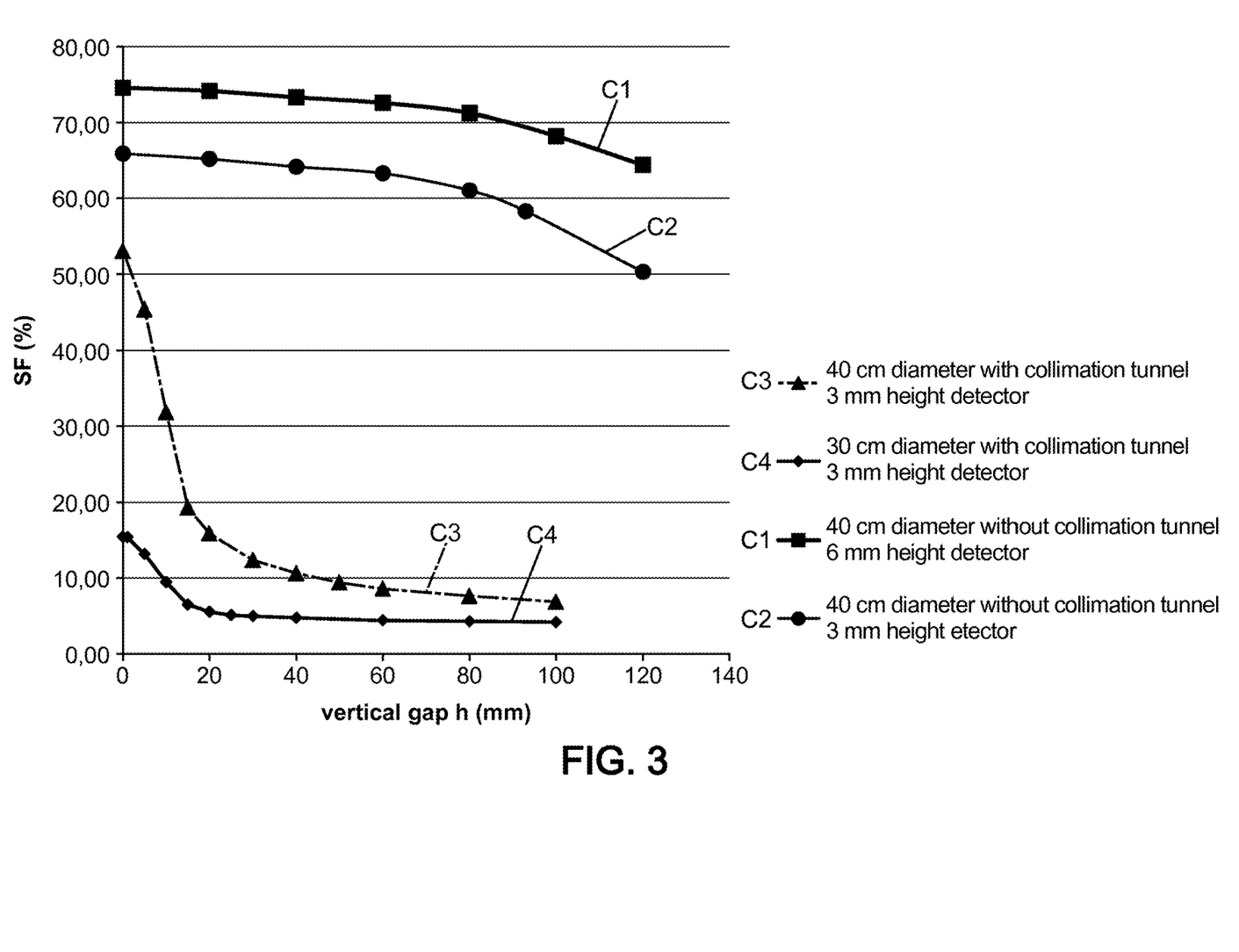
FIG. 3 shows examples of different curves obtained in different experimental conditions when performing a radiology method, showing the scattered fraction of signal received by the detectors as a function of the vertical gap existing between first and second vertical scanning.

FIG. 3 shows examples of different curves obtained in different experimental conditions when performing a radiology method, showing the scattered fraction of signal received by the detectors as a function of the vertical gap existing between first and second vertical scanning.

A first curve C1 shows the scattered fraction, expressed in percentage, of signal received by the detectors, which is a useless portion of received signal, as a function of the vertical gap existing between first and second vertical scanning, expressed in mm.

There are no collimation tunnels located upstream the detectors. The value of the height of the sensitive surfaces of the detectors is 6 mm. The value of the tension of the tube in the radiation sources is 120 kV. To simulate an overweight patient, a water bucket presenting a diameter of 40 cm has been used.

This curve C1 shows that the amount of scattered fraction is very high. This scattered fraction lowers a little bit for high values of vertical gap, for instance more than 10 cm. In these conditions, improvement coming from the vertical gap only is limited.

A second curve C2 shows the scattered fraction, expressed in percentage, of signal received by the detectors, which is a useless portion of received signal, as a function of the vertical gap existing between first and second vertical scanning, expressed in mm.

There are no collimation tunnels located upstream the detectors. The value of the height of the sensitive surfaces of the detectors is 3 mm. The value of the tension of the tube in the radiation sources is 120 kV. To simulate an overweight patient, a water bucket presenting a diameter of 40 cm has been used.

This curve C2 shows that the amount of scattered fraction is quite high, but not that high as for the curve C1. Therefore, limiting the height of the sensitive surfaces of the detectors has as a consequence the reduction of this scattered fraction. This scattered fraction lowers substantially, but only for high values of vertical gap, for instance more than 10 cm. In these conditions, improvement coming from the vertical gap only is still somewhat limited.

A third curve C3 shows the scattered fraction, expressed in percentage, of signal received by the detectors, which is a useless portion of received signal, as a function of the vertical gap existing between first and second vertical scanning, expressed in mm.

There are collimation tunnels located upstream the detectors. Those collimation tunnels present a depth having a value of 50 mm. The value of the height of the sensitive surfaces of the detectors is 3 mm. The value of the tension of the tube in the radiation sources is 120 kV. To simulate an overweight patient, a water bucket presenting a diameter of 40 cm has been used.

This curve C3 shows that the amount of scattered fraction becomes quite low, as soon as the vertical gap becomes substantial, even if still quite low. For instance, this scattered fraction is already quite low, less than 20%, as soon as the vertical gap becomes higher than 2 cm. However, without any vertical gap, i.e. with a vertical gap value of 0 mm, this scattered fraction is much higher, indeed more than 50%. With a height of sensitive surface of detectors of 6 mm, this positive effect is still there, even if a bit less important.

In these conditions of third curve C3, improvement coming from the vertical gap combined with collimation tunnels, appears to be much better than either vertical gap alone or collimation tunnels alone.

A fourth curve C4 shows the scattered fraction, expressed in percentage, of signal received by the detectors, which is a useless portion of received signal, as a function of the vertical gap existing between first and second vertical scanning, expressed in mm.

There are collimation tunnels located upstream the detectors. Those collimation tunnels present a depth having a value of 50 mm. The value of the height of the sensitive surfaces of the detectors is 3 mm. The value of the tension of the tube in the radiation sources is 95 kV. To simulate a standard patient, a water bucket presenting a diameter of 30 cm has been used.

This curve C4 shows that the amount of scattered fraction is relatively low even in the absence of vertical gap, but becomes even lower, as soon as the vertical gap becomes substantial, even if still quite low. For instance, this scattered fraction drops from 15% to 5%, as soon as the vertical gap becomes higher than 2 cm. With a height of sensitive surface of detectors of 6 mm, this positive effect is still there, even if a bit less important.

In these conditions of fourth curve C4, improvement coming from the vertical gap combined with collimation tunnels, appears to be better than either vertical gap alone or collimation tunnels alone, but this effect is much less for a standard patient, as represented on fourth curve C4, than for an overweight patient, as represented on third curve C3.

It can be deduced from curves C1 to C4, first that the combination of vertical gap and of collimation tunnels is very interesting and much better to reduce the scattered fraction that the separated effects of vertical gap alone and of collimation tunnels alone, and second that this scattered fraction reduction is all the more important that the patient is overweight.

The invention has been described with reference to preferred embodiments. However, many variations are possible within the scope of the invention.

The invention claimed is:

1. Method of radiography of an organ of a patient, comprising:
 a first vertical scanning of said organ by a first radiation source (1) and a first detector (3) cooperating to make a first two dimensional image of said organ,
 a second vertical scanning of said organ by a second radiation source (2) and a second detector (4) cooperating to make a second two dimensional image of said organ,
 said first vertical scanning and said second vertical scanning being performed synchronously,
 said first and second images viewing said organ of said patient according to different angles of incidence,
 wherein said method of radiography is performed with an overweight patient or with an obese patient,
 and wherein:

a first collimation tunnel (7) is located upstream said first detector (3), a second collimation tunnel (8) is located upstream said second detector (4), there is a vertical gap (h) between on the one hand said first source (1) and detector (3) and on the other hand said second source (2) and detector (4), such that said first vertical scanning and said second vertical scanning are performed synchronously but with a time shift in between, so as to reduce cross-scattering between said first and second images.

2. Method of radiography according to claim 1, wherein said collimation tunnel (7, 8) has a depth of more than 20 mm.

3. Method of radiography according to claim 1, wherein said vertical gap (h) is more than the height of the sensitive surface of any of the detectors (3, 4).

4. Method of radiography according to claim 3, wherein said vertical gap (h) is more than 10 mm.

5. Method of radiography according to claim 4, wherein said vertical gap (h) is less than 100 mm.

6. Method of radiography according to claim 3, wherein a height of the sensitive surface of both detectors ranges from 2 mm to 8 mm.

7. Method of radiography according to claim 1, wherein said vertical gap (h) is fixed.

8. Method of radiography according to claim 1, wherein said vertical gap (h) is tunable.

9. Method of radiography according to claim 8, wherein said vertical gap (h) is tunable according to patient morphology and/or according to patient organ.

10. Method of radiography according to claim 9, wherein said vertical gap (h) is tunable according to respective effective apertures of said sources (1, 2) and according to respective effective apertures of said detectors (3, 4), which said effective apertures are in turn tunable according to patient morphology and/or according to patient organ.

11. Method of radiography according to claim 1, wherein:

said vertical gap (h) does not exist at the very beginning of said first vertical scanning, but does exist at the very beginning of said second vertical scanning, said vertical gap (h) does not exist at the very end of said second vertical scanning, but does exist at the very end of said first vertical scanning.

12. Method of radiography according to claim 1, wherein said vertical gap (h) does always exist, even when neither said first vertical scanning nor said second vertical scanning are performed.

13. Method of radiography according to claim 1, wherein said patient morphology is chosen by a user of said method of radiography.

14. Method of radiography according to claim 1, wherein said patient morphology is determined by a scout view scanning at a reduced level of radiation.

15. Method of radiography according to claim 1, wherein collimators (5, 6) are located downstream said sources (1, 2).

16. Method of radiography according to claim 1, wherein said first and second images are perpendicular views of said organ.

17. Method of radiography according to claim 1, wherein said radiation sources (1, 2) are x-ray sources (1, 2) and said detectors (3, 4) are x-ray detectors (3, 4).

18. Method of radiography of an organ of a patient, comprising:

a first vertical scanning of said organ by a first radiation source (1) and a first detector (3) cooperating to make a first two dimensional image of said organ, a second vertical scanning of said organ by a second radiation source (2) and a second detector (4) cooperating to make a second two dimensional image of said organ, said first vertical scanning and said second vertical scanning being performed synchronously, said first and second images viewing said organ of said patient according to different angles of incidence, wherein there is a vertical gap (h) between on the one hand said first source (1) and detector (3) and on the other hand said second source (2) and detector (4), such that said first vertical scanning and said second vertical scanning are performed synchronously but with a time shift in between, so as to reduce cross-scattering between said first and second images.

19. Method of radiography according to claim 18, wherein said method of radiography is performed with an overweight patient or with an obese patient.

20. Method of radiography according to claim 18, wherein a collimation tunnel (7, 8) is located upstream each detector (3, 4) so as to further reduce cross-scattering on each image.

21. Method of radiography according to claim 20, wherein no scattering rejection grid is located upstream any detector (3, 4).

22. Method of radiography according to claim 18, wherein said detectors (3, 4) are geometrically linear detectors (3, 4).

23. Radiography apparatus comprising:

a first radiation source (1) and a first detector (3) cooperating to make a first two dimensional image of an organ of a patient, by performing a first vertical scan of said organ of said patient, a second radiation source (2) and a second detector (4) cooperating to make a second two dimensional image of said organ of said patient, by performing a second vertical scan of said organ of said patient, said sources (1, 2) and said detectors (3, 4) cooperating so as to perform said first vertical scanning and said second vertical scanning synchronously, said first and second images viewing said organ of said patient according to different angles of incidence, wherein there is a vertical gap (h) between on the one hand said first source (1) and detector (3) and on the other hand said second source (2) and detector (4), such that said first vertical scanning and said second vertical scanning are performed synchronously but with a time shift in between, so as to reduce cross-scattering between said first and second images.

24. Radiography apparatus according to claim 23, further comprising:

a first collimation tunnel (7) located upstream said first detector (3) so as to further reduce cross-scattering between said first and second images, a second collimation tunnel (8) located upstream said second detector (4) so as to further reduce cross-scattering between said first and second images.

* * * * *